United States Patent
Zhao et al.

(10) Patent No.: US 12,084,604 B2
(45) Date of Patent: Sep. 10, 2024

(54) HYDRATION-BASED SHAPE MEMORY ADHESIVE MATERIALS AND METHODS OF MAKING

(71) Applicant: Massachusetts Institute of Technology, Cambridge, MA (US)

(72) Inventors: Xuanhe Zhao, Allston, MA (US); Hyunwoo Yuk, Cambridge, MA (US); Heejung Roh, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/666,642

(22) Filed: Feb. 8, 2022

(65) Prior Publication Data
US 2022/0259463 A1    Aug. 18, 2022

Related U.S. Application Data

(60) Provisional application No. 63/148,874, filed on Feb. 12, 2021.

(51) Int. Cl.
*C09J 7/25* (2018.01)
*C09J 7/32* (2018.01)

(52) U.S. Cl.
CPC . *C09J 7/32* (2018.01); *C09J 7/25* (2018.01); *C09J 2301/12* (2020.08); *C09J 2301/306* (2020.08); *C09J 2301/414* (2020.08); *C09J 2405/00* (2013.01); *C09J 2433/00* (2013.01); *C09J 2475/006* (2013.01); *Y10T 428/28* (2015.01); *Y10T 428/2852* (2015.01)

(58) Field of Classification Search
None
See application file for complete search history.

(56) References Cited

U.S. PATENT DOCUMENTS

| | | | | |
|---|---|---|---|---|
| 5,964,744 | A * | 10/1999 | Balbierz | A61M 27/008 606/198 |
| 2009/0216170 | A1 | 8/2009 | Robinson | |
| 2015/0086791 | A1 | 3/2015 | Browne | |
| 2020/0353120 | A1 | 11/2020 | Zhao | |

OTHER PUBLICATIONS

A. J. Singer et al., Prospective, Randomized, Controlled Trial of Tissue Adhesive (2-Octylcyanoacrylate) vs Standard Wound Closure Techniques for Laceration Repair. Academic Emergency Medicine 5, 94-99 (1998).
P. Coulthard et al., Tissue adhesives for closure of surgical incisions. Cochrane Database of Systematic Reviews 5, CD004287 (2010).
T. B. Reece, T. S. Maxey, I. L. Kron, A prospectus on tissue adhesives. The American Journal of Surgery 182, S40-S44 (2001).
H. Khoshmohabat, S. Paydar, H. M. Kazemi, B. Dalfardi, Overview of agents used for emergency hemostasis. Trauma Monthly 21, (2016).
P. Hangge et al., Hemostasis and nanotechnology. Cardiovascular Diagnosis and Therapy 7, S267 (2017).
J. Yang, R. Bai, B. Chen, Z. Suo, Hydrogel adhesion: A supramolecular synergy of chemistry, topology, and mechanics. Advanced Functional Materials 30, 1901693 (2020).
G. M. Taboada et al., Overcoming the translational barriers of tissue adhesives. Nature Reviews Materials, 1-20 (2020).
G. C. Gurtner et al., Improving cutaneous scar formation by controlling the mechanical environment: large animal and phase I studies. Annals of Surgery 254, 217-225 (2011).
J. Li et al., Tough adhesives for diverse wet surfaces. Science 357, 378-381 (2017).
S. Blacklow et al., Bioinspired mechanically active adhesive dressings to accelerate wound closure. Science Advances 5, eaaw3963 (2019).
H. Yuk et al., Dry double-sided tape for adhesion of wet tissues and devices. Nature 575, 169-174 (2019).
V. W. Wong et al., A mechanomodulatory device to minimize incisional scar formation. Advances in Wound Care 2, 185-194 (2013).
A. Lendlein, R. Langer, Biodegradable, elastic shape-memory polymers for potential biomedical applications. Science 296, 1673-1676 (2002).
P. T. Mather, X. Luo, I. A. Rousseau, Shape memory polymer research. Annual Review of Materials Research 39, 445-471 (2009).
H. Meng, G. Li, A review of stimuli-responsive shape memory polymer composites. Polymer 54, 2199-2221 (2013).
F. N. Kelley, F. Bueche, Viscosity and glass temperature relations for polymer-diluent systems. Journal of Polymer Science 50, 549-556 (1961).
X. Mao, H. Yuk, X. Zhao, Hydration and swelling of dry polymers for wet adhesion. Journal of the Mechanics and Physics of Solids, 103863 (2020).
International Search Report for PCT/US22/15941 mailed Feb. 10, 2022.

* cited by examiner

*Primary Examiner* — Anish P Desai
(74) *Attorney, Agent, or Firm* — Nieves IP Law Group, LLC; Peter A. Nieves

(57) ABSTRACT

A dry shape memory adhesive material for adhering a target surface in the presence of fluid and for providing tunable mechanical contraction of an adhered surface. The dry shape memory adhesive material is pre-stretched and dried to provide an adhesive structure that implements a hydration-based shape memory mechanism to achieve both uniaxial and biaxial contractions of the adhered surface. According to preferred embodiments, the shape memory adhesive material includes a combination of one or more hydrophilic polymers or copolymers, one or more amine coupling group, and one or more cross linkers.

11 Claims, 12 Drawing Sheets

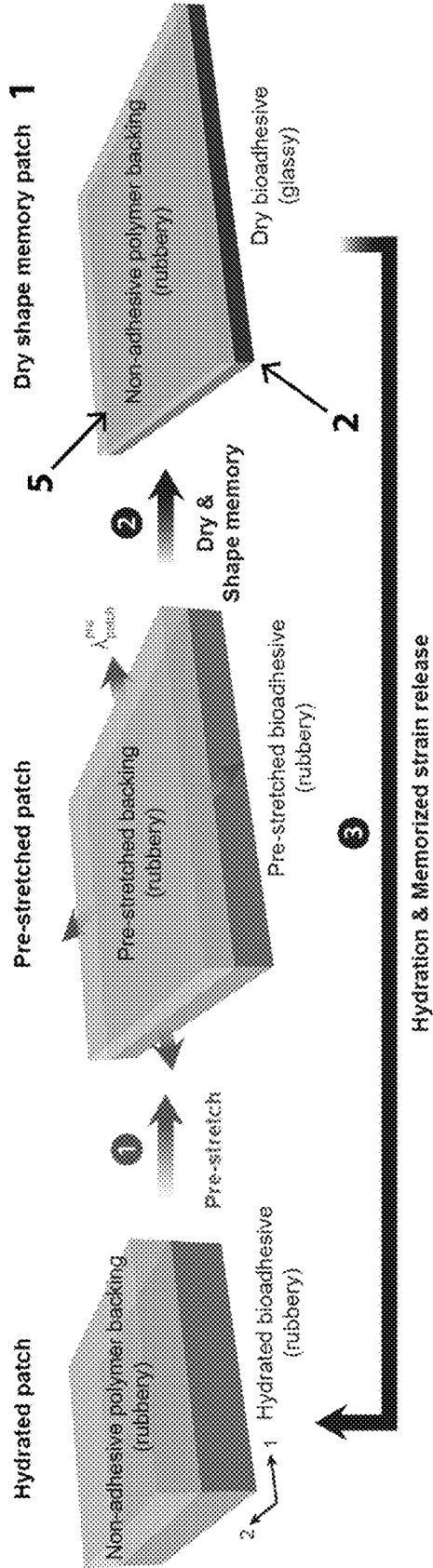
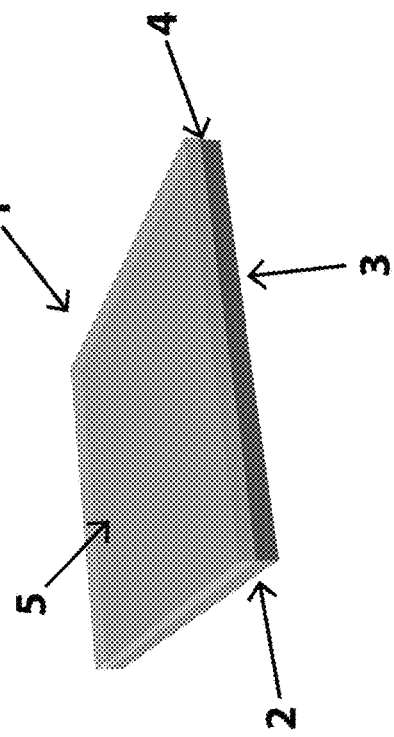
FIG. 1A
FIG. 1B

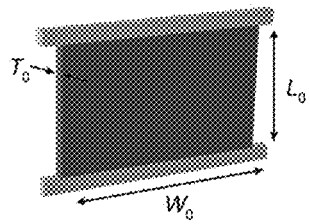
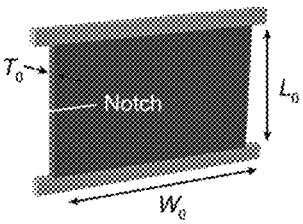
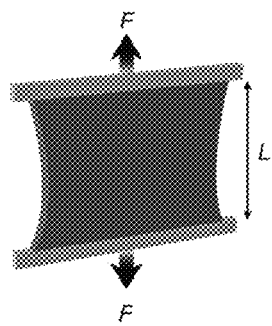
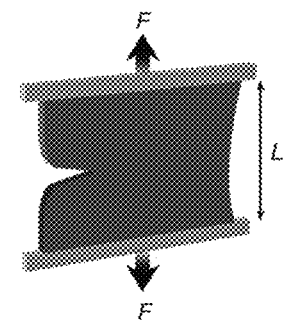
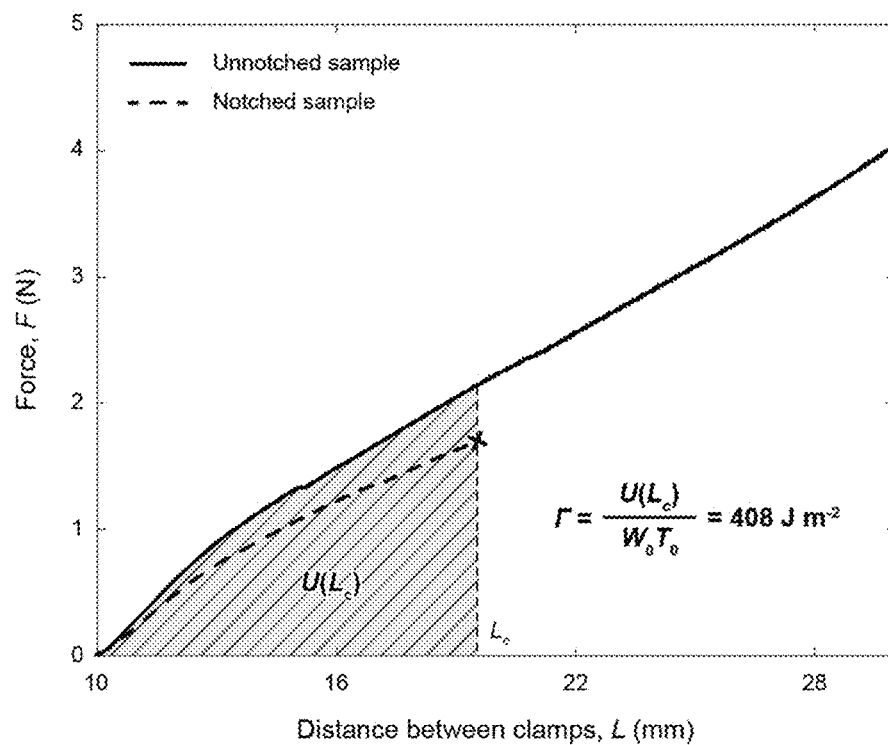

HYDRATION-BASED SHAPE MEMORY ADHESIVE MATERIALS AND METHODS OF MAKING

CROSS-REFERENCE TO RELATED APPLICATIONS

This application claims the benefit of priority to U.S. Provisional Patent Application No. 63/148,874, HYDRATION-BASED SHAPE MEMORY ADHESIVE MATERIALS AND METHODS OF MAKING, which was filed on Feb. 12, 2021. The disclosure of the prior application is incorporated by reference herein in its entirety.

STATEMENT OF GOVERNMENT SUPPORT

This invention was made with Government support under Grant No. D20AC00004 awarded by the Defense Advanced Research Projects Agency (DARPA). The Government has certain rights in the invention.

FIELD OF THE INVENTION

The present invention generally relates to materials and methods for adhering tissue, and more particularly to a shape memory adhesive material configured to provide rapid robust adhesion and tunable mechanical contraction of an adhered surface. The shape memory adhesive material is in the form of a pre-stretched and dried adhesive structure that implements a hydration-based shape memory mechanism to achieve both uniaxial and biaxial contractions of the adhered surface, particularly a wet tissue surface. According to preferred embodiments, the shape memory adhesive material includes a combination of one or more hydrophilic polymers or copolymers, one or more amine coupling group, and one or more cross linkers.

BACKGROUND OF THE INVENTION

Bioadhesives (e.g., tissue adhesives, hemostatic agents, and tissue sealants) have been demonstrated to provide several advantages over sutures and staples owing to their minimal tissue damage, air- and water-tight sealing, and ease of use. However, while sutures may be manually tightened to provide precise contracting and/or closing of target tissues on-demand, bioadhesives mostly serve as passive mechanical barriers or sealants without the capability of providing predictable and programmable mechanical modulation of underlying tissues. While some bioadhesives can be applied in a way that may provide limited mechanical contraction, such contraction is uncontrolled and without precise and predictive shape change. This absence of tunable mechanical modulation in existing bioadhesives results in various disadvantages including further swelling of the bioadhesives and subsequent dimensional changes (which can, for example, result in unwanted separation of underlying tissue), incomplete approximation of tissue edges, and unpredictable mechanical interaction between the tissue and the applied bioadhesive, etc. Further, unlike sutures and staples, commercially-available bioadhesives provide no or only weak and brittle adhesion to wet tissue surfaces (e.g., internal tissue surfaces or external surfaces covered by fluids such as blood and mucus). While a few blood-resistant tissue adhesives with improved adhesion performance have been developed, these typically require ultraviolet (UV) irradiation and/or prolonged steady pressure application (e.g., over 5 min) to form adhesion, thereby substantially limiting their utility in practical applications.

Thus, further improvements in both adhesive materials and methods of use are greatly needed.

SUMMARY OF THE INVENTION

The present invention provides a shape memory adhesive material that provides rapid robust adhesion and tunable mechanical contraction of an adhered surface.

According to one aspect, the present invention provides a dry shape memory adhesive material for adhering one or more target surfaces comprising a dry adhesive layer comprising one or more hydrophilic polymers, one or more amine coupling groups, and one or more cross linkers; the dry adhesive layer having a top surface, a bottom surface, a thickness measured from the top surface to the bottom surface, a length, and width; and the dry adhesive layer having a pre-stretched configuration in length and width that is greater in length and width than an original configuration prior to pre-stretching. Further, the dry shape memory adhesive material has a liquid content such that placement of one or more of the top and/or bottom surfaces of the dry adhesive layer in contact with the one or more target surfaces in the presence of fluid causes the dry adhesive layer to (a) absorb at least a portion of the fluid, swell in volume and transform to a hydrated rubbery state, and form of physical and covalent crosslinks on the one or more target surfaces, and (b) contract in length and/or width from the pre-stretched configuration to about the original configuration.

Embodiments according to these aspects can include one or more of the following features. The dry shape memory adhesive material further comprises at least one backing layer disposed on the top surface. The dry shape memory adhesive material further comprises a backing layer removably disposed on the bottom surface. The (i) one or more hydrophilic polymers are selected from polyacrylic acid, polyacrylamide, polyvinyl alcohol, polyhydroxy ethyl methacrylate, polyethylene glycol, poly vinyl pyrrolidone, poly styrene sulfonate, casein, albumin, gelatin, collagen, chitosan, hyaluronic acid, alginic acid, oxidized alginate, pectin, and combinations thereof. The (ii) one or more amine coupling groups are selected from N-hydroxysuccinimide ester, N-hydroxysulfosuccinimide ester, aldehyde, imidoester, epoxide, isocyanate, catechol, and combinations thereof. The (iii) one or more crosslinkers are selected from gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof. The backing layer is fabricated of one or more polyurethanes, silicone rubbers, styrene-butadiene-styrene copolymers, butyl rubbers, latex rubbers, and/or hydrogels. The dry adhesive layer comprises an interpenetrating network of chitosan and poly(acrylic acid) (PAA) grafted with N-hydroxysuccinimide (NHS) ester and one or more dry hydrophilic polyurethane backing layers disposed on one or more of the top and/or bottom surfaces of the dry adhesive layer. The adhesive layer has a Young's modulus in its hydrated rubbery state that is at least two orders of magnitude lower than the dry adhesive layer Young's modulus in the dry state. The dry shape memory adhesive material is in the form of a sheet, tape, patch, or film. The dry shape memory adhesive material is biodegradable.

According to another aspect, the present invention provides a method of forming a dry shape memory adhesive material having a pre-programmed contraction on hydration comprising: (i) forming an adhesive layer in a hydrated rubbery state having a top surface, a bottom surface, a first length, a first width, and a first thickness; (ii) disposing a polymer backing resin on the top surface of the adhesive layer; optionally (iii) before (ii) or after (ii), pre-stretching the adhesive layer in the hydrated rubbery state to provide the adhesive layer in the hydrated rubbery state with a second length greater than the first length, a second width greater than the first width, and a second thickness less than the first thickness; (iv) curing of the polymer backing resin to form a backing layer having a first backing layer length, a first backing layer width, and a first backing layer thickness, while maintaining the adhesive layer in the hydrated rubbery state; (v) pre-stretching the backing layer and adhesive layer in the hydrated rubber state in a length and/or thickness direction to apply a desired pre-programmed contraction in length and/or thickness on hydration; and (vi) drying the pre-stretched backing layer and adhesive layer to impart shape memory based on the pre-programmed contraction in length and/or thickness on hydration.

Embodiments according to these aspects can include one or more of the following features. Step (v) comprises pre-stretching the backing layer and adhesive layer in the hydrated rubber state in a length and thickness to provide (a) the backing layer with a second backing layer length greater than the first backing layer length, a second backing layer width greater than the first backing layer width, and a second backing layer thickness less than the first backing layer thickness, and (b) the adhesive layer in the hydrated rubber state with a third length greater than the second length, a third width greater than the second width, and a third thickness less than the second thickness. Step (v) pre-stretching is carried out by applying an equal amount of pre-stretch in both width and length directions, the equal amount of pre-stretch being measured as an equal multiple of pre-stretch based on width and length dimensions prior to step (v) pre-stretching to provide the dry shape memory adhesive material with isotropic pre-programmed contraction on hydration. Step (v) pre-stretching is carried out by applying an unequal amount of pre-stretch in width and length directions, the unequal amount of pre-stretch being measured as an equal multiple of pre-stretch based on width and length dimensions prior to step (v) pre-stretching to provide the dry shape memory adhesive material with anisotropic pre-programmed contraction on hydration.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principals of the invention.

FIGS. 1A-B schematically illustrate strain programming of a shape memory adhesive material by a hydration-based shape memory mechanism according to an embodiment of the present invention.

FIGS. 2A-D graphically illustrate mechanical properties of a shape memory adhesive material in the form of a patch having an elastomer backing layer and a bioadhesive layer according to an embodiment of the present invention, wherein FIG. 2A illustrates the nominal stress vs. stretch curves for a dry elastomer backing layer, FIG. 2B illustrates the nominal stress vs. stretch curves for a dry bioadhesive layer, FIG. 2C illustrates the nominal stress vs. stretch curves for a swollen elastomer backing layer, and FIG. 2D illustrates the nominal stress vs. stretch curves for a swollen bioadhesive layer.

FIGS. 4A-C graphically illustrate swelling of a shape memory adhesive patch according to embodiments of the present invention, where FIG. 4A illustrates swelling ratios of an elastomer backing layer and a bioadhesive layer in a wet physiological environment, FIG. 4B illustrates swelling mismatch canceling between an elastomer backing layer and bioadhesive layer in a shape memory bioadhesive patch, and FIG. 4C illustrates swelling canceling of a shape memory bioadhesive patch. Values in a represent the mean and the standard deviation (n=4). P values are determined by a Student's t test; ns, not significant.

FIGS. 5A-D illustrate the mechanical properties of a shape memory bioadhesive patch according to embodiments of the present invention, wherein FIGS. 5A-B show images of a dry shape memory bioadhesive patch (FIG. 5A) and a swollen shape memory bioadhesive patch (FIG. 5B), and FIG. 5C-D graphically illustrate nominal stress vs. stretch curves for a dry shape memory bioadhesive patch (FIG. 5C) and a swollen shape memory bioadhesive patch (FIG. 5D).

FIGS. 6A-C illustrate fracture toughness of shape memory bioadhesive patch according to an embodiment of the present invention, wherein FIGS. 6A-B schematically illustrate pure-shear tests for an unnotched sample (FIG. 6A) and a notched sample. (FIG. 6B), and FIG. 6C graphically illustrate force vs. distance between clamps for the unnotched and notched swollen shape memory bioadhesive patches for fracture toughness measurement. $L_c$ indicates the critical distance between the clamps at which the notch turns into a running crack. The measured fracture toughness of the shape memory bioadhesive patch is 408 J m$^{-2}$.

FIG. 8A shows theoretical and experimental values of $\lambda_{patch}^{shrink}$ vs. $\lambda_{patch}^{pre}$ for isotropically shape memory bioadhesive patches, and FIG. 8B shows theoretical and experimental values of $\lambda_{patch}^{shrink}$ vs. $\lambda_{patch}^{pre}$ for anisotropically shape memory bioadhesive patches. Values represent the mean and the standard deviation (n=4).

FIGS. 10A-D schematically illustrate mechanical testing setups for evaluation of adhesion performance, wherein FIG. 10A illustrates a testing setup for interfacial toughness measurements based on the standard 180-degree peel test (ASTM F2256), FIG. 10B illustrates a testing setup for shear strength measurements based on the standard lap-shear test (ASTM F2255), FIG. 10C illustrates a testing setup for wound closure strength measurements based on the standard tensile test (ASTM F2458-05), and FIG. 10D illustrates a testing setup for burst strength measurements based on the standard tensile test (ASTM F2392-04).

FIGS. 11A-D graphically illustrate adhesion performance of a shape memory bioadhesive patch according to embodiments of the present invention, wherein FIG. 11A shows interfacial toughness, FIG. 11B shows shear strength, FIG. 11C shows wound closure strength, and FIG. 11D shows burst strength of the shape memory bioadhesive patch on wet porcine skin. Values represent the mean and the standard deviation (n=4).

DETAILED DESCRIPTION

Figure 2A:
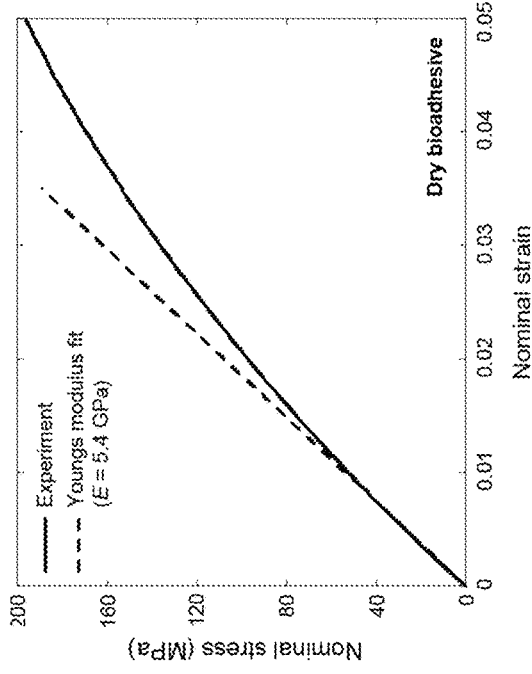
Figure 2B:
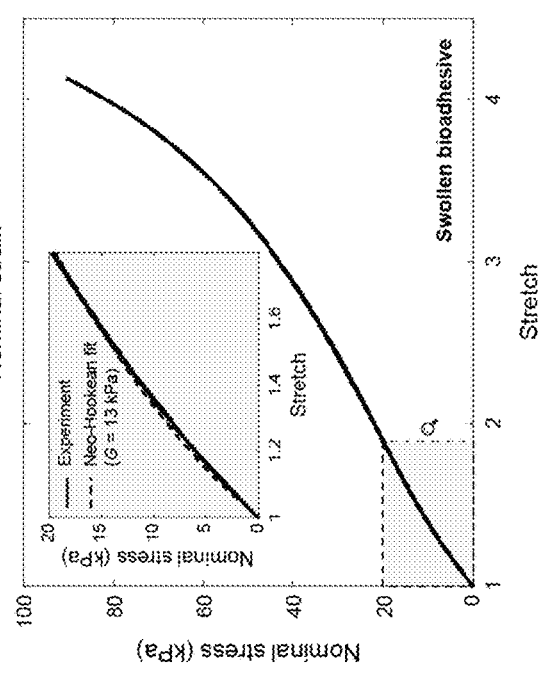
Figure 2C:
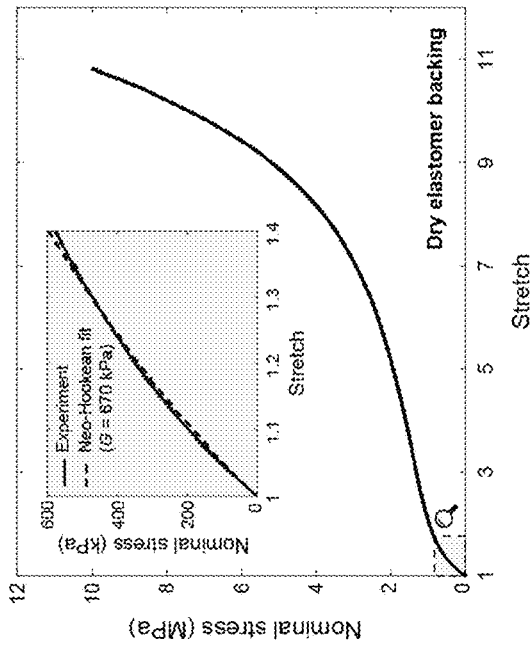
Figure 2D:
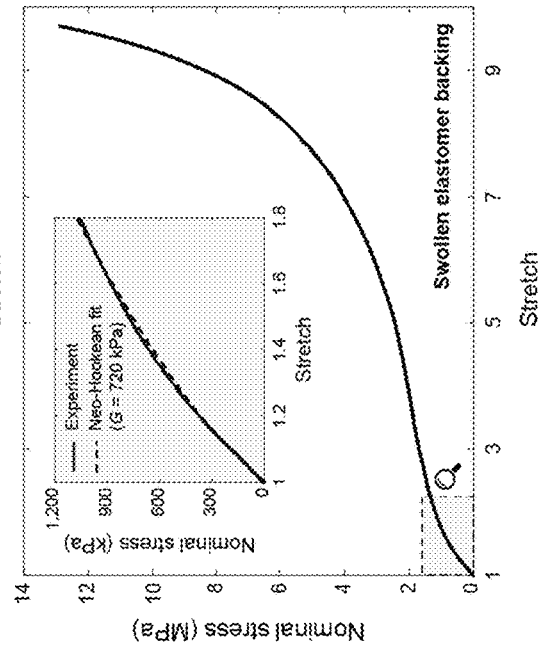

The following definitions are useful for interpreting terms applied to features of the embodiments disclosed herein, and are meant only to define elements within the disclosure.

As used herein, the term "shape memory adhesive material" refers to a single or multi-layered shape memory adhesive material and which includes at least an adhesive layer. The "shape memory adhesive material" may include one or more backing layers disposed on one or more surfaces of the adhesive layer. The "shape memory adhesive material" may be in the form of a film, patch, tape, strip, sheet, or the like, and, as such, may be referred to interchangeably as a "shape memory adhesive patch", a "shape memory adhesive tape", a "shape memory adhesive film", a "shape memory adhesive strip", a "shape memory adhesive sheet", etc. depending on its form.

As used herein, the term "patch", "tape", "film", "strip", and "sheet", when describing the adhesive material of the present invention refers to a structure that has a relatively large area as compared to thickness. Such a structure provides flexibility, which can be particularly beneficial when applied to surfaces which move, bend, stretch, twist, etc. such as various tissue surfaces of a living body.

As used herein, the term "dry" when describing the adhesive material, the adhesive layer, and the backing layer of the present invention refers to a material or layer that is below the equilibrium moisture content of the material or layer in use. As such, when a dry adhesive material, a dry adhesive layer, and a dry backing layer of the present invention are placed in contact with fluid, such as a wet tissue or other wet or wetted (e.g., wetted by saline) surface to which it will adhere, the dry adhesive material, dry adhesive layer, and dry backing layer will absorb the fluid (e.g., water, saline, moisture, and physiological body fluids such as blood plasma, interstitial fluid, lymphatic fluid, cerebrospinal fluid, and gastrointestinal fluid) from the wet or wetted surface. Generally, a dry adhesive material, dry adhesive layer, and dry backing layer will have less than about 50% by weight of liquid components based on total weight of the dry material or layer.

As used herein, the term "rubbery" when used to describe states of the adhesive layer and backing layer of the present invention refers to materials having mechanical properties and behaviors of elastomeric rubbers, such as low Young's modulus, elastic recovery after release (or removing) of stretch, etc.

As used herein, the term "glassy" when used to describe states of the adhesive layer and backing layer of the present invention refers to materials having mechanical properties and behaviors that of plastics, such as high Young's modulus, and plastic deformation after release (or removing) of stretch, etc.

As used herein, the term "absorb" when describing the mechanism by which the dry adhesive material, dry adhesive layer, and dry backing layer absorb fluid (e.g., water, saline, moisture, and physiological body fluids such as blood plasma, interstitial fluid, lymphatic fluid, cerebrospinal fluid, and gastrointestinal fluid) from a wet surface in which it is placed in contact with, refers to atoms or molecules from the fluid entering the dry adhesive material, dry adhesive layer, and dry backing layer.

As used herein, the term "body fluid" refers to aqueous physiological fluids including blood, saliva, gastrointestinal fluid, lymphatic fluid, cerebrospinal fluid, gastrointestinal fluid, and mucus.

As used herein, the terms "wet surface" and "wet tissue" refers to a surface, including biological tissues, that contain or are covered with fluid including water, saline, moisture, and physiological body fluids such as blood plasma, saliva, mucus, interstitial fluid, lymphatic fluid, cerebrospinal fluid, and gastrointestinal fluid.

As used herein, the term "covered", when used to describe the surface to which the adhesive material is applied as being "covered" with fluid, refers to a surface that is partially or completely covered with fluid. As such, "covered" can include a configuration in which an entire layer of fluid is disposed on the surface that the adhesive material is applied to such that, upon application of the adhesive material, a layer of fluid separates the entire adhesive material from the surface. "Covered" can also include a configuration in which only a portion (less than 100% but greater than 50%) of a surface to which the adhesive material is applied has a layer of fluid disposed therein, such that one or more portions of the adhesive material are separated from the surface by the fluid and one or more portions of the adhesive material are in direct contact with the surface.

As used herein, "swelling" when used to describe the pre-stretched dry adhesive material, pre-stretched dry adhesive layer, and pre-stretched dry backing layer refers to absorption of fluid by the pre-stretched dry adhesive material, pre-stretched dry adhesive layer, and pre-stretched dry backing layer and swelling upon contact with the fluid and/or one or more wet surfaces. Such "swelling" generally refers to an increase in water contents and the subsequent increase in total volume by the pre-stretched dry adhesive material, pre-stretched dry adhesive layer, and pre-stretched dry backing layer.

As used herein, the term "contraction", when used to describe the pre-stretched dry adhesive material, pre-stretched dry adhesive layer, and pre-stretched dry backing layer refers to a decrease in size in the length and width directions upon absorption of fluid by the pre-stretched dry adhesive material, pre-stretched dry adhesive layer, and pre-stretched dry backing layer.

As used herein, the terms "rapid and predictive contraction" and "predictable mechanical contraction", when used to describe the shape memory adhesive material itself as well as the effect of the shape memory adhesive on one or more target surfaces refers to contraction that is "rapid" in that it occurs within about 3 minutes, preferably within less than about 1 minute; and that is "predictable" in that the amount of contraction in size is achievable within about 20% error from the prescribed predicted change in size, preferably within about than 10% error from the prescribed predicted change in size, particularly within less than 10% error from the prescribed predicted change in size.

As used herein, the term "bioadhesive" when used to describe the dry bioadhesive material refers the capability of the material to form adhesion on the surface of biological tissues.

As used herein, "biodegradable" when used to describe the adhesive material refers the decomposition and/or subsequent removal of the adhesive material in part or whole within a living animal by the endogenous enzymes and/or water inside the animal.

As used herein, the term "instant" when used to describe the instant temporary physical crosslinks between the adhesive material and one or more target surfaces refers to a time elapse from the instant that the adhesive material makes contact with the one or more target surfaces of greater than zero seconds and up to or within about one minute, more preferably less than or equal to about 50 seconds, more preferably less than or equal to about 40 seconds, more preferably less than or equal to about 30 seconds, more preferably less than or equal to about 20 seconds, more preferably less than or equal to about 15 seconds, more preferably less than or equal to about 10 seconds, more preferably less than or equal to about 9 seconds, more preferably less than or equal to about 8 seconds, more preferably less than or equal to about 7 seconds, more preferably less than or equal to about 6 seconds, and more preferably less than or equal to about 5 seconds.

As used herein, the term "temporary" when used to describe the instant temporary physical crosslinks between the adhesive material and one or more target surfaces refers to a time range extending between time at which the instant temporary physical crosslinks form and a sufficiently long time such as over 24 hours after which the instant temporary physical crosslinks form.

As used herein, "rapid" or "quick" when used to describe the fast covalent crosslinking between the adhesive material and one or more target surfaces refers to a time elapse from the instant that the adhesive material makes contact with the one or more target surfaces of greater than zero seconds and up to and including 5 minutes, more preferably less than or equal to about 4.5 minutes, more preferably less than or equal to about 4 minutes, more preferably less than or equal to about 3.5 minutes, more preferably less than or equal to about 3 minutes, more preferably less than or equal to about 2.5 minutes, more preferably less than or equal to about 2 minutes, more preferably less than or equal to about 1.5 minutes, and more preferably less than or equal to about 1 minute.

As used herein, the term "physical crosslinks", when used to describe the interaction between the adhesive material and the one or more target surfaces whose adhesion is sustained by one or more types of physical interactions including but not limited to hydrogen bonds, electrostatic bonds, van der Waals interactions, $\pi$-$\pi$ bonds, and hydrophobic interactions.

As used herein, the term "covalent crosslinks", when used to describe the interaction between the adhesive material and the one or more target surfaces whose adhesion is sustained by one or more types of covalent chemical bonds including but not limited to carbon-carbon bonds, carbon-nitrogen bonds, carbon-oxygen bonds, carbon-sulfide bonds, and silicon-oxygen bonds.

As used herein, the term "rapid", when used to describe the rapid adhesion provided by the adhesive material, refers to a time greater than zero seconds and up to and including 5 minutes, more preferably less than or equal to about 4.5 minutes, more preferably less than or equal to about 4 minutes, more preferably less than or equal to about 3.5 minutes, more preferably less than or equal to about 3 minutes, more preferably less than or equal to about 2.5 minutes, more preferably less than or equal to about 2 minutes, more preferably less than or equal to about 1.5 minutes, and more preferably less than or equal to about 1 minute. This time is measured from the instant that the adhesive material is applied to the target surface and gentle pressure applied to the time that the adhesive material is adhered. The formation of the adhesion can be experimentally determined by a simple pulling test and visual inspection, wherein the adhesive material does not separate from the target surface when pulled.

As used herein, the term "gentle", when used to describe the pressure applied to the adhesive material, refers to a pressure of no greater than about 50 kPa, for example ranging from about 1 kPa to about 50 kPa. For example, a gentle pressure would refer to a pressure of no greater than about 45 kPa, no greater than about 40 kPa, no greater than about 35 kPa, no greater than about 30 ka, no greater than about 25 kPa, no greater than about 20 kPa, no greater than about 15 kPa, no greater than about 10 kPa, no greater than about 8 kPa, no greater than about 6 kPa, no greater than about 5 kPa, no greater than about 4 kPa, no greater than about 3 kPa, no greater than about 2 kPa, and even as low as about 1 kPa. According to an exemplary embodiment, a suitable gentle pressure is about 10 kPa.

As used herein, the term "tough", when describing the adhesion formed by the adhesive material, refers to an interfacial toughness of at least about 100 J m$^{-2}$, 120 J m$^{-2}$, 140 J m$^{-2}$, 160 J m$^{-2}$, 180 J m$^{-2}$, 200, J m$^{-2}$, 220 J m$^{-2}$, 240 J m$^{-2}$, at least about 250 J m$^{-2}$, at least about 260 J m$^{-2}$, at least about 270 J m$^{-2}$, at least about 280 J m$^{-2}$, at least about 290 J m$^{-2}$, and even values of at least about 300 J m$^{-2}$.

As used herein, the term "strong", when describing the adhesion formed by the adhesive material, refers to a shear or tensile strengths of at least about 10 kPa, at least about 20 kPa, at least about 30 kPa, at least about 40 kPa, at least about 50 kPa, at least about 60 kPa, and at least about 70 kPa.

As used herein, the term "robust", when describing the adhesion formed by the adhesive material on a target surface, refers collectively to the toughness and strength of the adhesion, including measurements of interfacial toughness over 100 J m$^{-2}$, shear strength over 30 kPa, and tensile strength over 10 kPa, and in a preferred embodiment, an interfacial toughness of at least about 240 J m$^{-2}$, shear strength of at least about 70 kPa and tensile of at least about 50 kPa.

As used herein, the term "flexible", when describing the shape memory adhesive material, refers a property of thin material in the form of patch, tape, film, strip, or sheet that can physically be twisted and/or bent at the minimum radius of curvature less than 10 mm, preferably less than 5 mm, without mechanical failure.

The present invention generally provides a shape memory adhesive material that is capable of rapid and predictive contraction upon adhesion to one or more target surfaces, particularly tissue surfaces. In embodiments of the invention, the shape memory adhesive material is in the form of a dry shape memory adhesive material fabricated so as to provide a dry-crosslinking mechanism for instant strong adhesion in the presence of fluid. According to embodiments, the dry shape memory adhesive material incorporates a hydration-based shape memory mechanism to achieve rapid robust adhesion and predictable mechanical contraction upon application to one or more target surfaces.

Reference will now be made in detail to embodiments of the present invention, examples of which are illustrated in the accompanying drawings. Wherever possible, the same reference numbers are used in the drawings and the description to refer to the same or like parts.

According to one aspect, the present invention provides a shape memory adhesive material 1 that includes at least an adhesive layer 2 having a bottom surface 3 and a top surface 4. Preferably, the adhesive layer 1 is generally in the form of a sheet, tape, patch, or film (all of which may be perforated, partially perforated, or not perforated). The adhesive layer 1 generally comprises a combination of one or more hydrophilic polymers or copolymers, one or more amine coupling groups, and one or more cross linkers. More particularly, the adhesive layer 1 is in the form of a pre-stretched dry adhesive layer (FIGS. 1 and 3) comprising a combination of (i) one or more hydrophilic polymers or copolymers that absorbs water at dry state grafted with amine-coupling groups, and (ii) crosslinkers.

According to embodiments of the present invention, the (i) one or more hydrophilic polymers or copolymers are selected from any conventional hydrophilic polymers that absorb water at a dry state, including, but not limited to polyacrylic acid, polyacrylamide, polyvinyl alcohol, polyhydroxy ethyl methacrylate, polyethylene glycol, poly vinyl pyrrolidone, poly styrene sulfonate, polyurethane, casein, albumin, gelatin, collagen, chitosan, hyaluronic acid, alginic acid, oxidized alginate, pectin, cellulose, oxidized cellulose, and combinations thereof. Because the present adhesive material can be used in a wide variety of biomedical applications, the polymers used in the present invention are preferably biocompatible (although for non-biomedical applications it would not be necessary to utilize only biocompatible polymer materials). According to preferred embodiments, the one or more hydrophilic polymers contain one or more negatively-charged groups such as poly (acrylic acid), casein, albumin, and alginic acid, whose negatively-charged groups endow hygroscopic properties that are desirable for rapid absorption and removal of interfacial liquid on wet surfaces.

According to embodiments of the present invention, the (ii) one or more amine coupling groups are selected from conventional amine coupling groups, including but not limited to, N-hydroxysuccinimide ester, N-hydroxysulfosuccinimide ester, aldehyde, imidoester, epoxide, isocyanate, catechol, and combinations thereof. Because the present adhesive material can be used in a wide variety of biomedical applications, the amine coupling groups used in the present invention are preferably biocompatible (although for non-biomedical applications it would not be necessary to utilize only biocompatible amine coupling groups). Such amine coupling groups are configured such that the one or more hydrophilic polymers can be grafted with the one or more amine-coupling groups, and such that the one or more amine coupling groups subsequently form covalent crosslinks with the wet/wetted surface on which the adhesive material is used.

According to embodiments of the present invention, the (iii) one or more crosslinkers are selected from conventional crosslinkers, including but not limited to gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof. Because the present adhesive material can be used in a wide variety of biomedical applications, the crosslinkers used in the present invention are preferably biocompatible (although for non-biomedical applications it would not be necessary to utilize only biocompatible crosslinkers).

According to the present invention, the adhesive layer 2 is in the form of a pre-stretched dry layer such that, when it is placed into contact with one or more target surfaces in the presence of fluid (e.g., wet tissue), it absorbs fluid, causing the dry layer to swell. Absorption of fluid and swelling of the dry adhesive layer 2 provides instant temporary crosslinking between the adhesive layer 2 (particularly between carboxylic acid groups, hydroxyl groups, sulfonic acid groups, amine groups, and catechol groups in the adhesive layer 2) and the tissue surface, and further allows for fast subsequent covalent coupling or crosslinking between the one or more amine coupling groups (e.g., NHS ester groups, sulfo-NHS ester groups, aldehyde groups, imidoester groups, epoxide groups) and the one or more surfaces via amine groups naturally present in the tissue surface. Pre-stretching of the adhesive layer 2 is provided such that, when the adhesive layer 2 is placed in contact with one or more target surfaces in the presence of fluid (e.g., wet tissue), it absorbs fluid triggering the hydration-based shape memory mechanism described herein in further detail.

The shape memory adhesive 1 may further include one or more removable or integrated (non-removable) backing layers 5 disposed upon the bottom surface 3 and/or top surface 4 of the adhesive layer 2. For example, one or more backing layers 5 may be disposed upon the bottom surface 3 and/or top surface 4, particularly to aid in handling the shape memory adhesive material 1 and to provide protection against moisture and unwanted adhesion. Preferably, backing layers 5 are disposed to cover the entire surfaces 4,3 of the adhesive layer 2 on which they are disposed. However, if desired, the backing layer 5 can be configured to cover only a portion of (or one or more portions of) the surfaces 4, 3 on which they are disposed, while leaving one or more portions of the surfaces 4, 3 exposed.

Figure 3:
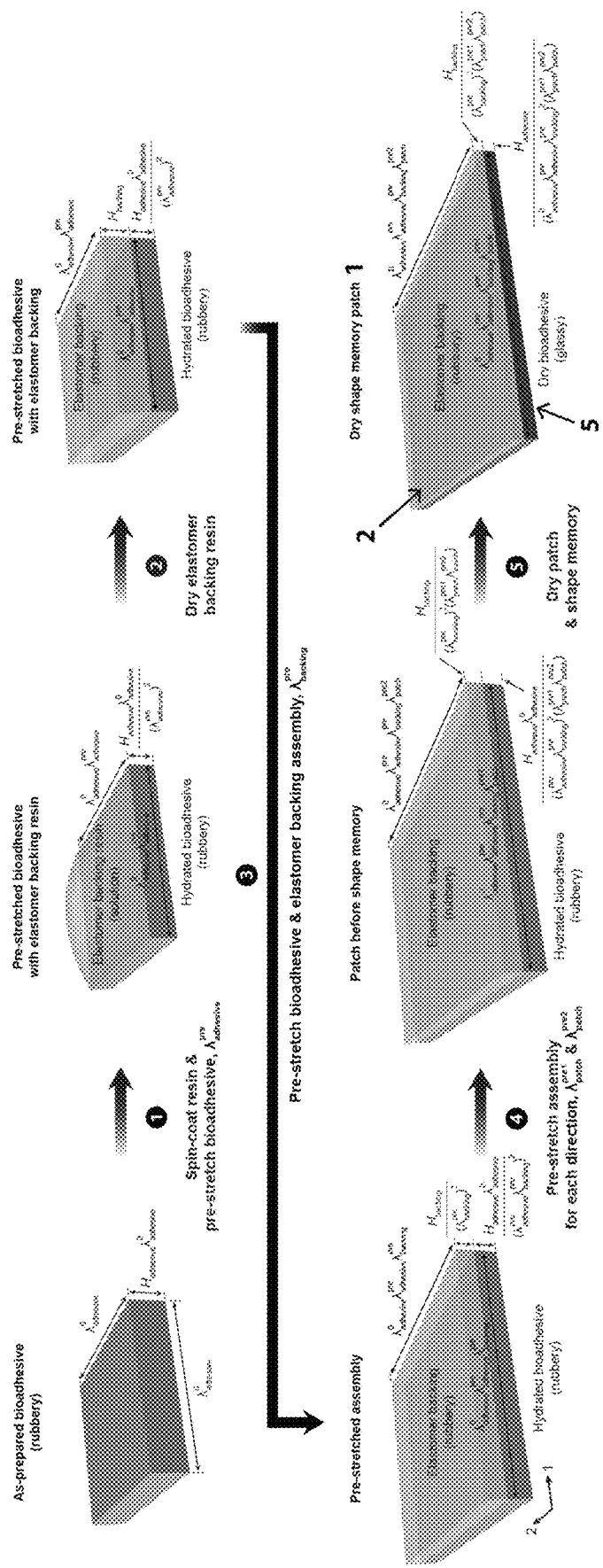
FIG. 3 schematically illustrates a hydration-based shape memory fabrication process according to an embodiment of the present invention, where Step (1) spin-coats an elastomer backing resin layer on an as-prepared bioadhesive layer and pre-stretches the as-prepared bioadhesive covered with uncured elastomer backing resin $\lambda_{adhesive}^{pre}$, Step (2) dries the elastomer backing resin layer while keeping the bioadhesive layer hydrated, Step (3) pre-stretches the bioadhesive layer and elastomer backing layer assembly $\lambda_{backing}^{pre}$, Step (4) pre-stretches the bioadhesive patch for each direction, and Step (5) dries the bioadhesive patch to thereby provide a shape memory bioadhesive patch.

According to an exemplary embodiment, the shape memory adhesive 1 includes a backing layer 5 disposed on the top surface 4 of the adhesive layer 2 (e.g., as shown in FIGS. 1 and 3). The bottom surface 3 of the adhesive layer 2 may be exposed (i.e., not provided with a backing layer 5) or, if desired, may be provided with a removable backing layer 5. During use, the exposed bottom surface 3 of the adhesive layer 2 is placed in contact with the target surface for adhesion. If a backing layer 5 is provided on the bottom surface 3, it may be removed prior to use to expose the bottom surface 3. For single-sided adhesion (i.e., adhesion to a target surface on only the bottom surface 3 of the adhesive layer 2), the backing layer 5 provided on the top surface 4 is in the form of a non-adhesive layer that protects the top surface 4 (or one or more portions of the top surface 4) from adhering to surfaces during use. In this embodiment, this backing layer 5 on the top surface may be in the form of an integrated backing layer or a removable backing layer 5 which is not removed prior to or during use.

According to embodiments where double-sided adhesion is desired, the backing layer 5 may be completely or partially omitted from the shape memory adhesive material 1, or may be provided on the top surface 4 and/or bottom surface 3 and removed prior to use to expose the bottom and top surfaces 3, 4, which could then be sandwiched between multiple target surfaces for adhesion to the surfaces.

In some applications, it may be desirable to have a combination of one or more removable and one or more integrated backing layers 5 disposed on a single surface so that the adhesive properties of only those portions of the surface with the removable backing layer 5 disposed thereon may be used by removing the removable backing layer 5 from those portions, while the adhesive properties of those portions of the surface with the integrated backing layer 5 disposed thereon are not utilized. For example, a central portion of a bottom surface 3 of an adhesive layer 2 may have an integrated backing layer disposed thereon, while portions of the bottom surface 3 surrounding the central portion may have one or more removable backing layers disposed thereon (not shown). This will provide a configuration in which the bottom surface 3 of the adhesive layer 2 will adhere to a target surface along an outside portion or perimeter of the adhesive layer 2 upon removal of the removable backing layers 5, while a central portion of the adhesive layer 2 will not adhere due to the integrated backing layer 5 which is not removed. Embodiments of the present invention further include any other suitable configurations of removable and integrated backing layers 5 based on a particular use and target surface.

The backing layers 5 are generally provided so as to prevent adhesion of the underlying adhesive layer 2 to a surface prior to the intended time of use and/or to prevent adhesion of the underlying adhesive layer 2 (e.g., adhesion of a top or bottom surface 4, 3) to a non-target surface while the adhesive material 1 is in use. As such, the backing layer 5 is one which blocks the adhesive properties of the adhesive layer 2. Because adhesion is triggered by contacting the adhesive layer 2 with a fluid, the backing layer 5 can generally be fabricated of any material that prevents liquid from coming into contact with the underlying adhesive layer 2. According to embodiments of the invention, the backing layer 5 is a pre-stretched dry polymer backing layer (FIGS. 1 and 3) fabricated of a biocompatible material that is non-adhesive to wet surfaces, such as wet tissue surfaces. Some exemplary polymeric materials suitable for use in forming the non-adhesive backing layer 5 include, but are not limited to, polyurethanes, silicone rubbers, styrene-butadiene-styrene copolymers, butyl rubbers, latex rubbers, and hydrogels.

In an exemplary embodiment, the present invention shape memory adhesive material 1 comprises one or more dry non-adhesive polymer backing layers 5 formed of hydrophilic polyurethane disposed on one or more surfaces 3,4 of a dry adhesive layer 2 formed of an interpenetrating network of chitosan and poly(acrylic acid) (PAA) grafted with N-hydroxysuccinimide (NETS) ester.

According to the present invention, the shape memory adhesive material 1 is provided with a hydration-based shape memory mechanism configured to achieve fast and precisely tunable mechanical contraction. The hydration-based shape memory mechanism relies on significant mechanical modulus changes of the hydrogels (forming the adhesive layer 2) in the hydrated rubbery state and the dry glassy state. Generally, the adhesive layer 2 demonstrates a particular Young's modulus in its dry state, while it demonstrates several orders of magnitudes lower Young's modulus when in its swollen hydrated rubbery state. For example, in one embodiment, the adhesive layer 2 exhibits a Young's modulus around 5.4 GPa in the dry state while it exhibits a Young's modulus of 36 kPa (equivalent to shear modulus of 12 kPa) when swollen in physiological saline (e.g., see FIG. 2). By utilizing the hydration-based shape memory mechanism, the non-adhesive polymer backing layer 5 and the adhesive layer 2 forming the shape memory adhesive material 1 are pre-stretched in their hydrated state (i.e., the rubbery state where mechanical properties and behaviors are that of elastomeric rubbers such as low Young's modulus, elastic recovery after release of stretch, etc.) to a prescribed amount in each direction (particularly length and width), and then the pre-stretched adhesive material 1 is dried into its dry and stable state (i.e., the glass state where mechanical properties and behaviors are that of plastics such as high Young's modulus, plastic deformation after release of stretch, etc) to provide the shape memory properties (e.g., see FIG. 1).

Once hydrated by fluid (e.g., water or other physiological fluids including saline, interstitial fluid, and intracellular fluid from wet tissues), the shape memory adhesive material 1 rapidly transforms from the dry glass state to its hydrated rubber state (typically within less than about 3 minutes, in some embodiments less than about 2 minutes, and in some embodiments less than about 1 minute) and contracts by the elastic recovery of the memorized pre-stretch. Simultaneously, hydration of the shape memory adhesive material 1 also activates the dry-crosslinking mechanism of the adhesive layer 2 to form rapid and robust adhesion by the removal of any interfacial water or other physiological fluids present on the target surface, followed by the formation of physical and covalent crosslinks on the target surface.

According to various embodiments, one or more layers of the shape memory adhesive material 1, such as an adhesive layer 2 and/or backing layer 5, contains one or more therapeutic agents for delivery during use. In particular, one or more therapeutic agents can be contained within the adhesive layer 2 hydrogel composition for release into underlying tissue and/or wound. As such, the present invention shape memory adhesive material 1 can further serve as a versatile drug delivery platform capable of prolonged and stable release of therapeutic agents to an underlying target surface.

Fabrication of the Shape Memory Adhesive Material

Figure 4B:
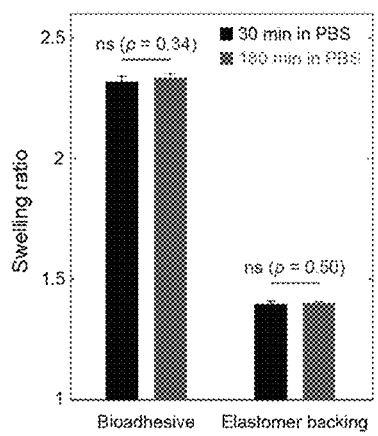
Figure 4C:
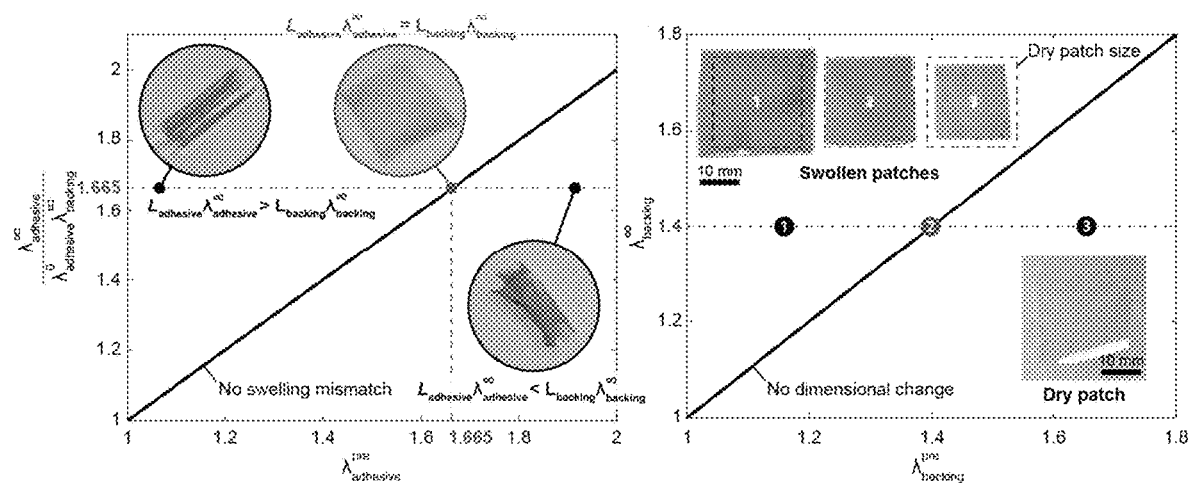

Based on the present invention hydration-based shape memory mechanism, the shape memory adhesive material 1 is fabricated through a process of multiple steps of pre-stretch and drying processes (e.g., see FIG. 3). Since both the dry backing layer(s) 5 and dry adhesive layer 2 forming the shape memory adhesive material 1 are configured to absorb fluid and based on their individual properties will swell in a wet physiological environment to varying degrees (as demonstrated by FIGS. 4A-C), the fabrication process of the shape memory adhesive material 1 was divided into five steps.

Initially, the as-prepared shape memory adhesive material 1 in the rubber state has the dimension of $\lambda_{adhesive}^{0}$ in length and width and $H_{adhesive}\lambda_{adhesive}^{0}$ in thickness. The following five step process was then carried out.

Step 1. The non-adhesive polymer backing resin layer 5 (i.e., before curing) is disposed on the as-prepared adhesive layer 2 (e.g., by spin coating, spray coating, dip coating, silk-printing, direct ink writing, etc), and the adhesive layer 2 is pre-stretched with $\lambda_{adhesive}^{pre}$ to cancel out the swelling mismatch between the non-adhesive polymer backing layer 5 and the adhesive layer 2 (Step 1 in FIG. 3). After this step, the resulting adhesive layer 2 in the rubbery state has the dimension of $\lambda_{adhesive}^{0}\lambda_{adhesive}^{pre}$ adhesive in length and width and $(H_{adhesive}\lambda_{adhesive}^{0})(\lambda_{adhesive}^{pre})$ in thickness. It is noted that while the polymer backing resin layer 5 is disposed on the adhesive layer 2 during this pre-stretching step, this backing resin layer 5 is uncured and, thus, in a fluid or resin state. As such, the backing resin layer 5 is not considered to be "pre-stretched" but rather, flows in its fluid state during pre-stretching of the adhesive layer 2. Thus, no pre-stretch properties are imparted on the uncured backing resin layer 5 in this step. If desired, in some embodiments of Step 1, the adhesive layer 2 is pre-stretched prior to disposing the non-adhesive polymer backing resin layer 5 on the adhesive layer 2.

Step 2. The non-adhesive polymer backing layer 5 is cured on the pre-stretched adhesive layer 2 (Step 2 in FIG. 3). The curing of the non-adhesive polymer backing can be achieved by conventional curing mechanisms, including but not limited to evaporation of solvent in resin, thermal curing, irradiation of high-energy light (e.g., ultraviolet light), and chemical curing by crosslinking agents. In particular, this curing of the backing layer 5 is carried out while keeping the adhesive layer 2 in a hydrated state using any suitable means that will prevent excessive evaporation of solvent (e.g., water). For example, the excessive evaporation of solvent can be prevented by performing the process in chamber with high humidity (e.g., over 80% relative humidity), performing the process quickly (e.g., within less than 10 minutes), or a combination of both. After this step, the non-adhesive polymer backing layer 5 in the rubbery state has the dimension of $\lambda_{adhesive}^{0}\lambda_{adhesive}^{pre}$ in length and width and $H_{backing}$ in thickness; the adhesive layer 2 in the rubbery state has the dimension of $\lambda_{adhesive}^{0}\lambda_{adhesive}^{pre}$ in length and width and $(H_{adhesive}\lambda_{adhesive}^{0})(\lambda_{adhesive}^{pre})^{-2}$ in thickness.

Step 3. Both the non-adhesive polymer backing layer 5 and the adhesive layer 2 are pre-stretched in length and/or width directions, with $\lambda_{backing}$ to cancel out the dimensional change of the adhesive material 1 by swelling in wet physiological environment (Step 3 in FIG. 3). After this step, the where pre-stretching in both length and width is carried out, the non-adhesive polymer backing layer 5 in the rubbery state has the dimension of $\lambda_{adhesive}^{0}\lambda_{adhesive}^{pre}\lambda_{backing}^{pre}$ in length and width and $(H_{backing})(\lambda_{backing}^{pre})^{-2}$ in thickness; the adhesive layer 2 in the rubbery state has the dimension of $\lambda_{adhesive}^{0}\lambda_{adhesive}^{pre}\lambda_{backing}^{pre}$ in length and width and $(H_{adhesive}\lambda_{adhesive}^{0})(\lambda_{adhesive}^{pre}\lambda_{backing}^{pre})^{-2}$ in thickness. In embodiments in which pre-stretching is carried out in Step 3 only in length or only in width (but not both) directions, only that direction in which pre-stretching is carried out would be provided with the above-modified dimensions.

Step 4. Both the non-adhesive polymer backing layer 5 and adhesive layer 2 are pre-stretched with $\lambda_{patch}^{pre1}$ and $\lambda_{patch}^{pre2}$ in length and/or width directions to apply the desired amount of contractions for each direction in which pre-stretching is carried out (Step 4 in FIG. 3). After this step, for embodiments in which pre-stretching is carried out in both the length and width directions, the non-adhesive polymer backing layer 5 in the rubbery state has the dimension of $\lambda_{adhesive}^{0}\lambda_{adhesive}^{pre}\lambda_{backing}^{pre}\lambda_{patch}^{pre1}$ in length $\lambda_{adhesive}^{0}\lambda_{adhesive}^{pre}\lambda_{backing}^{pre}\lambda_{patch}^{pre2}$ in width, and $(H_{backing})((\lambda_{backing}^{pre})^{2}\lambda_{patch}^{pre1}\lambda_{patch}^{pre2})^{-1}$ in thickness; the adhesive layer 2 in the rubbery state has the dimension of $\lambda_{adhesive}^{0}\lambda_{adhesive}^{pre}\lambda_{backing}^{pre}\lambda_{patch}^{pre1}$ in length, $\lambda_{adhesive}^{0}\lambda_{adhesive}^{pre}\lambda_{backing}^{pre}\lambda_{patch}^{pre2}$ in width, and $(H_{adhesive}\lambda_{adhesive}^{0})$ $((\lambda_{adhesive}^{pre}\lambda_{backing}^{pre})^{2}\lambda_{patch}^{pre1}\lambda_{patch}^{pre2})^{-1}$ in thickness. In embodiments in which pre-stretching is carried out in Step 4 only in length or only in width (but not both) directions, only that direction in which pre-stretching is carried out would be provided with the above-modified dimensions. Further, only the direction(s) in which pre-stretching is carried out in Step 4 will be provided with shape memory (i.e., contraction on hydration/fluid absorption will only occur in the pre-stretched directions). Thus, for example, in embodiments in which Step 4 includes pre-stretching in both length and width directions, upon hydration/fluid absorption, the shape memory adhesive material 1 will contract in both length and width. On the other hand, if pre-stretching is carried out only in a length direction, upon hydration/fluid absorption, the shape memory adhesive material 1 will contract in only the length direction.

Step 5. The pre-stretched adhesive material 1 is dried to impart the shape memory based on the pre-stretched configuration (Step 5 in FIG. 3). After this step, the non-adhesive polymer backing layer 5 in the rubbery state has the dimension of $\lambda_{adhesive}^{0}\lambda_{adhesive}^{pre}\lambda_{backing}^{pre}\lambda_{patch}^{pre1}$ in length $\lambda_{adhesive}^{0}\lambda_{adhesive}^{pre}\lambda_{backing}^{pre}\lambda_{patch}^{pre2}$ in width, and $(H_{backing})((\lambda_{backing}^{pre})^{2}\lambda_{patch}^{pre1}\lambda_{patch}^{pre2})^{-1}$ in thickness; the adhesive layer 2 in the glassy state has the dimension of $\lambda_{adhesive}^{0}\lambda_{adhesive}^{pre}\lambda_{backing}^{pre}\lambda_{patch}^{pre1}$ in length, $\lambda_{adhesive}^{0}\lambda_{adhesive}^{pre}\lambda_{backing}^{pre}\lambda_{patch}^{pre2}$ in width, and $(H_{adhesive})((\lambda_{adhesive}^{0}\lambda_{adhesive}^{pre}\lambda_{backing}^{pre})^{2}\lambda_{patch}^{pre1}\lambda_{patch}^{pre2})^{-1}$ in thickness.

It is noted that while the above-described five step process is a preferred process for imparting the desired shape memory properties in the adhesive material 1, in some embodiments fewer than all five steps can be carried out which include the fundamental processes for pre-stretching and drying which impart the desired hydration-based shape memory properties. It is also noted that the five step process can generally be carried out as outlined, but with some adjustment to the order in which steps/sub-steps are carried out. One skilled in the art can, thus, use the five step process as a general guideline and, if desired, can modify the order and/or inclusion of specific steps to achieve specific shape-memory properties.

For example, in some embodiments, it may be desirable to provide shape-memory (contraction) in certain layers of the adhesive material 1 but not all layers. As such, the steps can be modified to only provide pre-stretching steps in those specific layer(s). For example, it may not be necessary in some applications to impart hydration-based shape memory to the cured backing layer 5 and, thus, only pre-stretching of the adhesive layer 2 to impart shape-memory on the adhesive layer 2 is needed (with any additional pre-stretching process to impart shape-memory on the backing layer 5 eliminated). According to another alternate embodiment, Step 3, which is carried out to cancel out dimensional change of the adhesive material 1 can generally be achieved to a desired degree during the Step 4 pre-stretching. As such, in some embodiments, Step 3 can be skipped. In particular, Step 3 accounts for the possibility that both the adhesive layer 2 and the backing layer(s) 5 will generally swell when exposed to fluid, which generally results in an increase in volume but may also result in increases in length, width, and/or thickness (this can result in an increase in different degrees depending on specific properties of each material). Thus, Step 3 can be provided as a separate step to introduce "non-swelling" characteristic to the shape-memory adhesive. In connection with this, in some embodiments, the present invention provides an adhesive in which swelling upon absorption of fluid is canceled out by carrying out Step 3 tailored to achieve this result, skipping Step 4 (and, thus, skipping imparting the contraction shape-memory properties to the adhesive), and proceeding directly to Step 5.

According to the present invention, it is possible to pre-program either isotropic or anisotropic shape memory in the adhesive material 1 based on the pre-stretching conditions. In particular, in Step 5, if pre-stretching is carried out for both length and width directions, and the pre-stretch in each direction is equal (wherein an "equal" pre-stretch is defined as an equal multiple or percent of stretch of the original dimension, e.g., wherein length and width are both pre-stretched to 2× their original dimension), then isotropic shape memory contraction is pre-programmed. If, on the other hand, if the pre-stretch for the length and width directions are not equal (e.g., a greater pre-stretch in length than in width, such as a pre-stretch in length of 2× the original length dimension and a pre-stretch in width of 1.5× the original width dimension), then anisotropic shape memory contraction is pre-programmed. In another embodiment, an extreme case of anisotropic shape memory contraction is pre-programmed by only carrying out one direction of pre-stretch (e.g., stretching only in length and not in width, or only in width and not in length) such that there is no contraction except in the single direction of pre-stretch.

According to an exemplary embodiment, the swelling ratio of the as-prepared adhesive layer 2 is $\lambda_{adhesive}^{0}=1.48$, the equilibrium swelling ratio of the adhesive layer 2 is $\lambda_{adhesive}^{\infty}=3.46$, the equilibrium swelling ratio of the non-adhesive polymer backing layer 5 is $\lambda_{backing}^{\infty}=1.4$, the pre-stretch ratio to cancel out the swelling mismatch is $\lambda_{adhesive}=(\lambda_{adhesive}^{\infty})(\lambda_{adhesive}^{0}\lambda_{backing}^{\infty})^{-1}=1.665$, and pre-stretch ratio to cancel out the swelling of the shape memory adhesive material 1 is $\lambda_{baking}^{pre}=\lambda_{backing}^{\infty}=1.4$. It is noted that different choices of adhesive layer 2 and non-adhesive polymer backing layer 5 compositions can be suitably be substituted by implementing appropriate values corresponding to each composition.

According to various embodiments, one or more layers of the shape memory adhesive material 1, such as an adhesive layer 2 and/or backing layer 5, contains one or more therapeutic agents for delivery during use. In particular, one or more therapeutic agents can be contained within the adhesive layer 2 hydrogel composition for release into underlying tissue and/or wound. As such, the present invention shape memory adhesive material 1 can further serve as a versatile drug delivery platform capable of prolonged and stable release of therapeutic agents to wounds while, at the same time, facilitating healing and closure of the wounds through the pre-programmed contraction.

Tunable Mechanical Contraction of the Shape Memory Adhesive Material

Figure 5A:
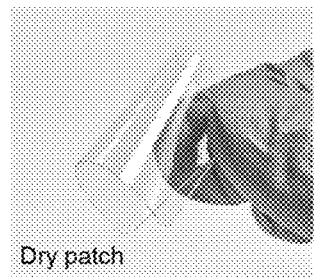
Figure 5B:
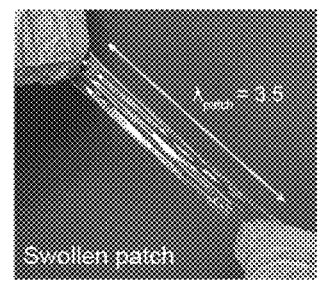
Figure 5C:
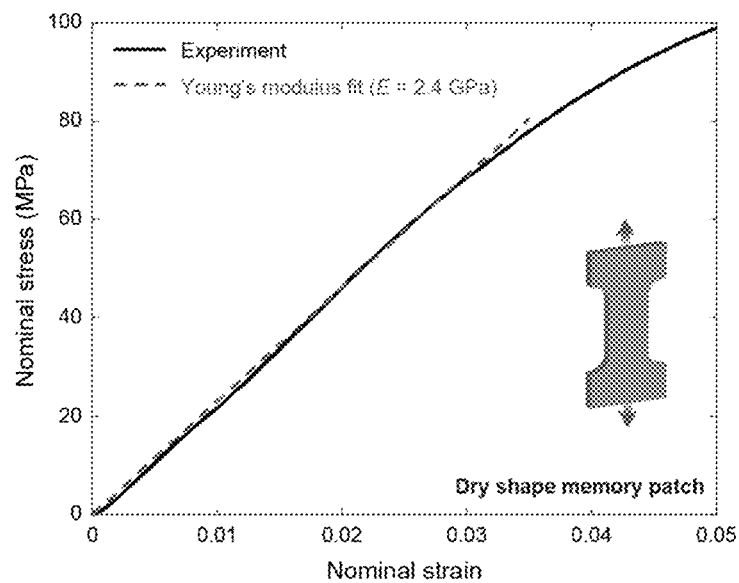
Figure 5D:
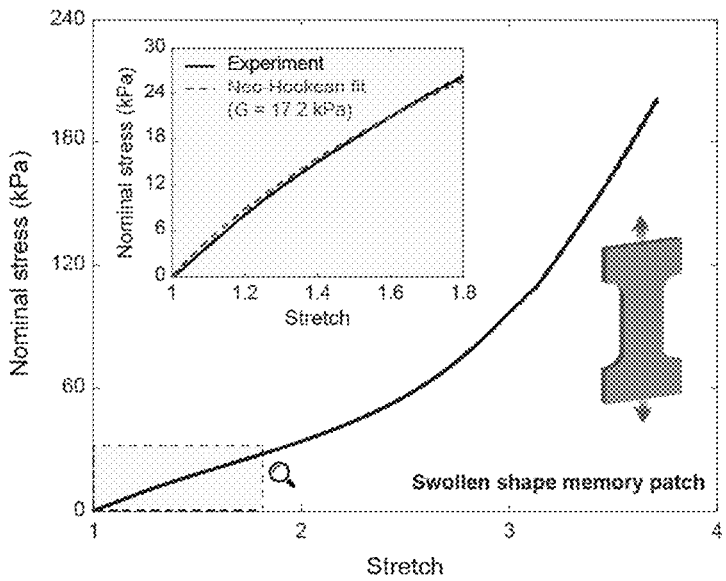
Figure 7:
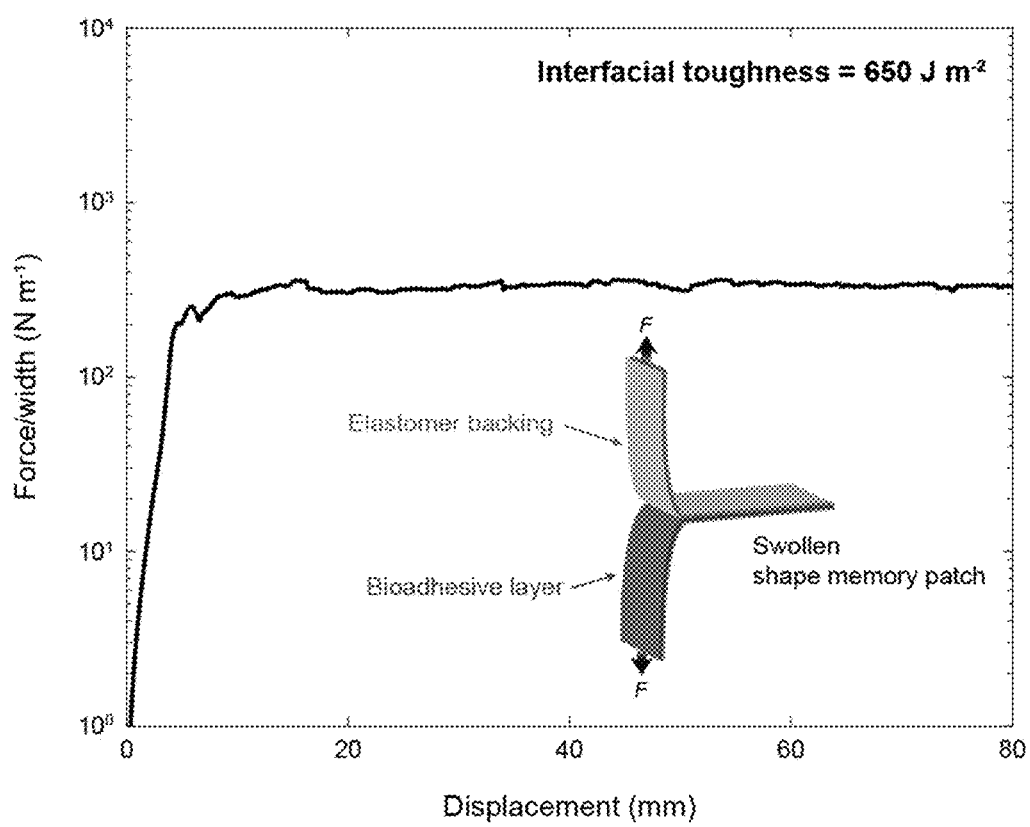
FIG. 7 graphically illustrates interfacial toughness between an elastomer backing layer and bioadhesive layer in a shape memory bioadhesive patch according to an embodiment of the present invention, wherein the measured interfacial toughness between a swollen elastomer backing layer and bioadhesive layer is 650 J m$^{-2}$.

In the dry state, the shape memory adhesive material 1 is a flexible film due to the glassy adhesive layer 2 (e.g., with Young's modulus of about 100 MPa to about 10 GPa) (see FIG. 5A and C). Once hydrated and swollen (e.g., when provided in a wet physiological environment), the shape memory adhesive material 1 becomes stretchable (ultimate tensile stretch at least over 2 times, preferably over 3 times of the original length) and soft (Young's modulus less than 1 MPa, equivalent to shear modulus of less than 333 kPa (shear modulus of about ⅓ Young's modulus) hydrogel due to the dry glass to hydrated rubbery transition of the hydrated adhesive layer 2 (see FIGS. 5B and D). Furthermore, the shape memory adhesive material 1 demonstrates a high fracture toughness of at least about 300 J m$^{-2}$, in some embodiments at least about 350 J m$^{-2}$, and in an exemplary embodiment at least about 400 J m$^{-2}$ (See FIGS. 6A-C) and high interfacial toughness between the non-adhesive polymer backing and the bioadhesive layer over 600 J m$^{-2}$ (FIG. 7) that provide robust mechanical property against mechanical failures.

Figure 8A:
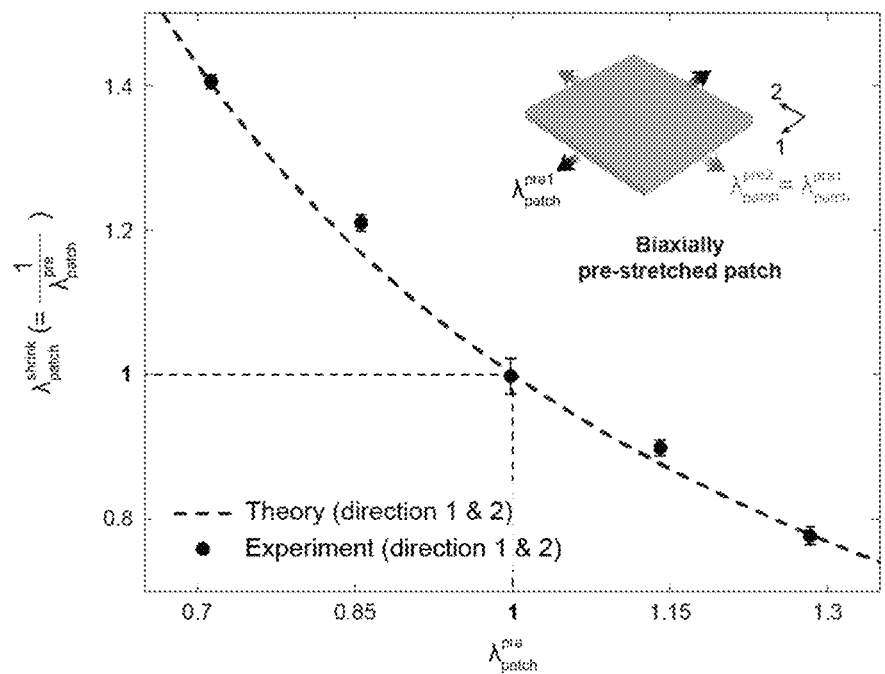
FIGS. 8A-B graphically illustrate the predictable mechanical contraction of the shape memory bioadhesive patch according to embodiments of the present invention, where
Figure 8B:
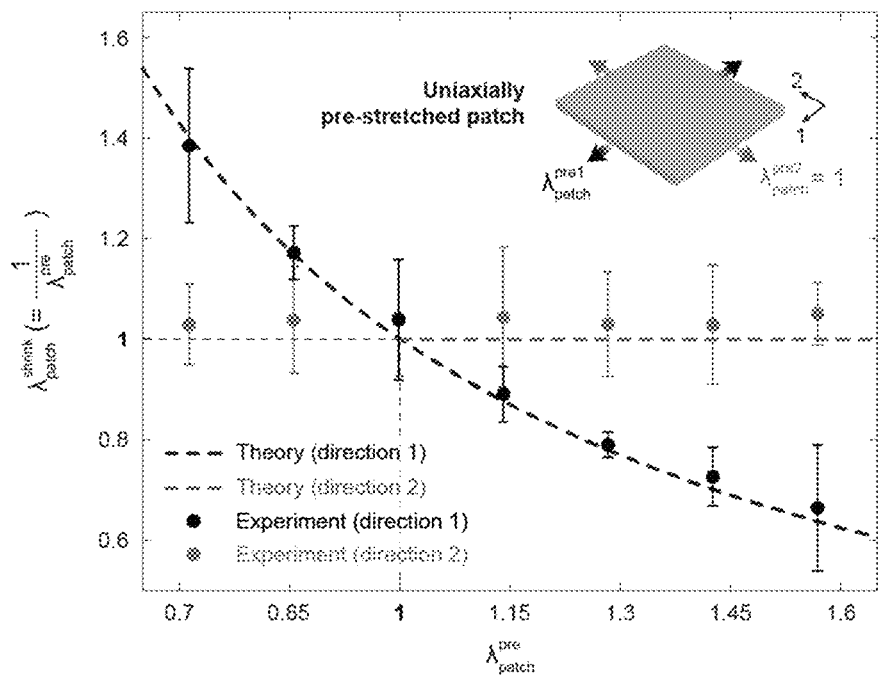
Figure 9A:
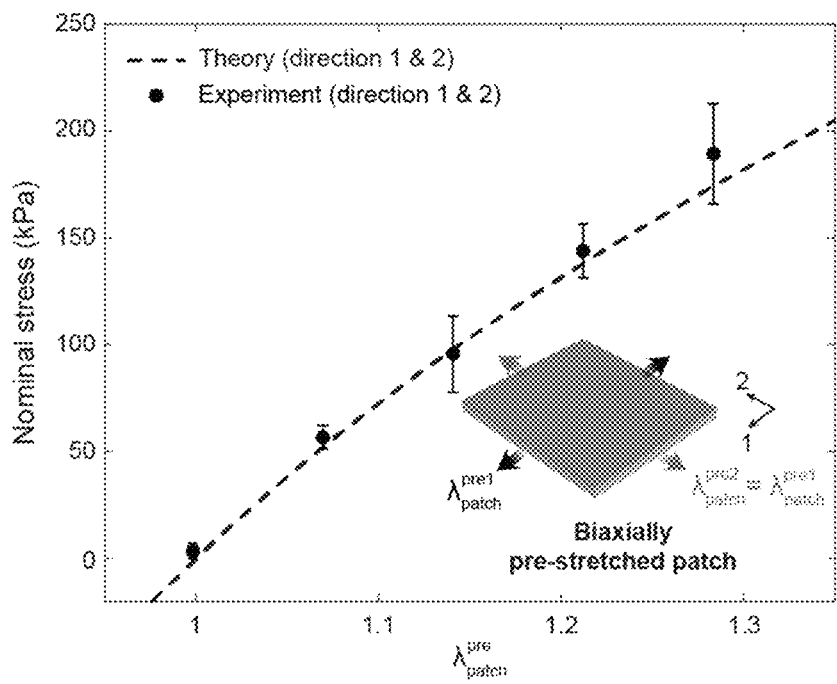
FIGS. 9A-B graphically illustrate contractile stress generated by shape memory bioadhesive patches according to embodiments of the present invention, wherein experimental and theoretical values for the nominal contractile stress vs. $\lambda_{patch}^{pre}$ generated by the isotropically (FIG. 9A) and the anisotropically (FIG. 9B) strain programmed shape memory bioadhesive patches. Values represent the mean and the standard deviation (n=4).
Figure 9B:
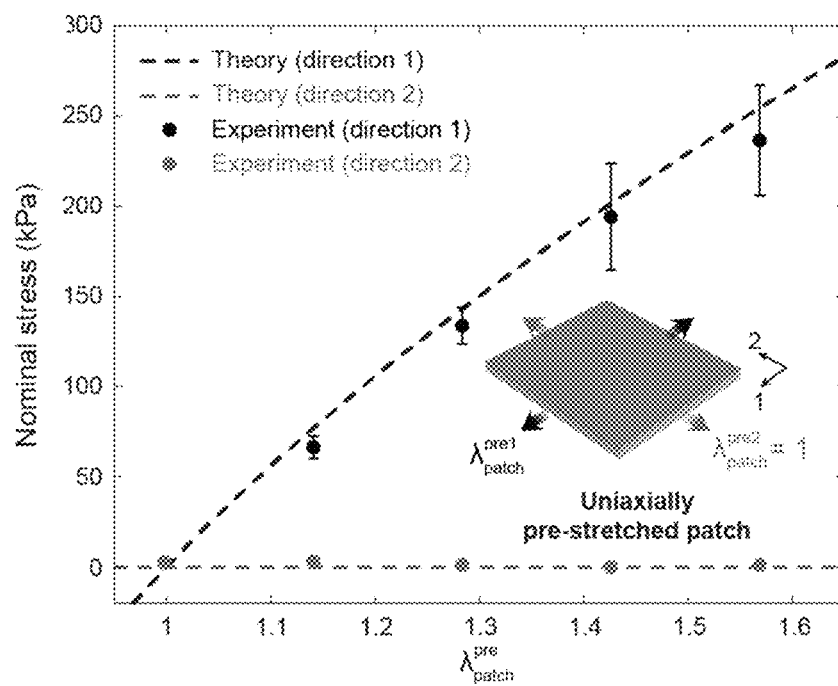
Figures 10A, 10B, 10C, 10D:
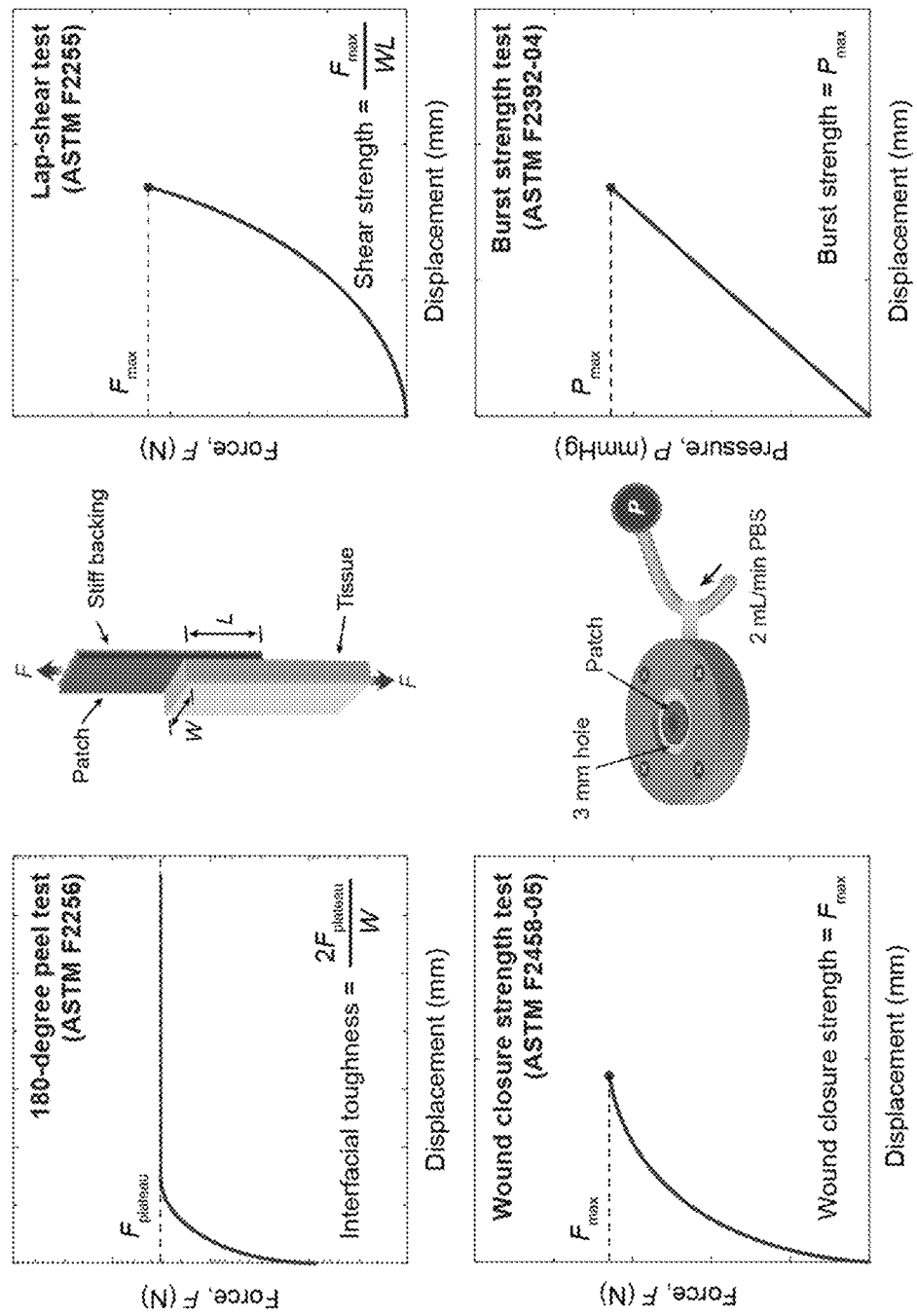
Figure 11A:
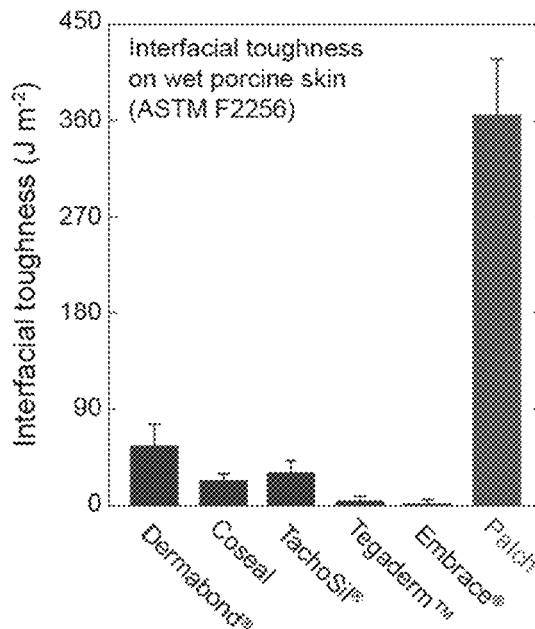
Figure 11B:
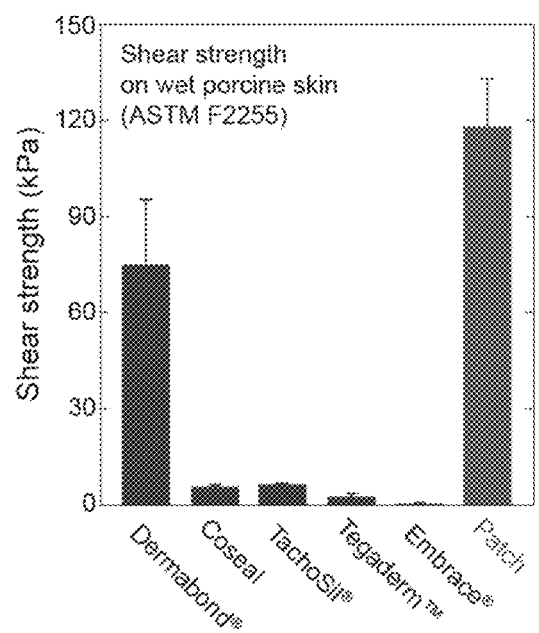
Figure 11C:
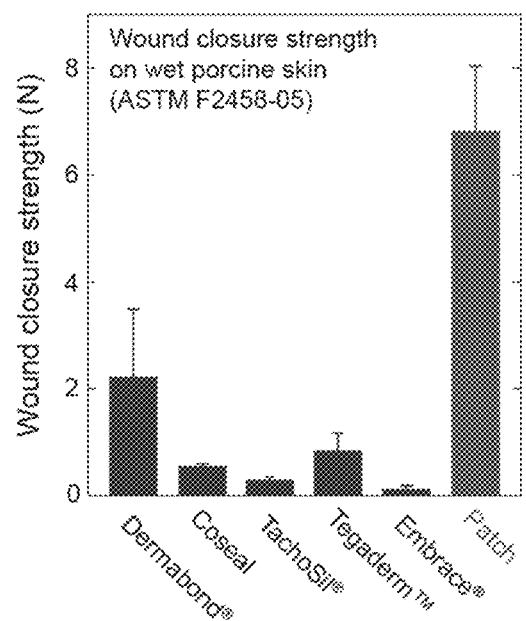
Figure 11D:
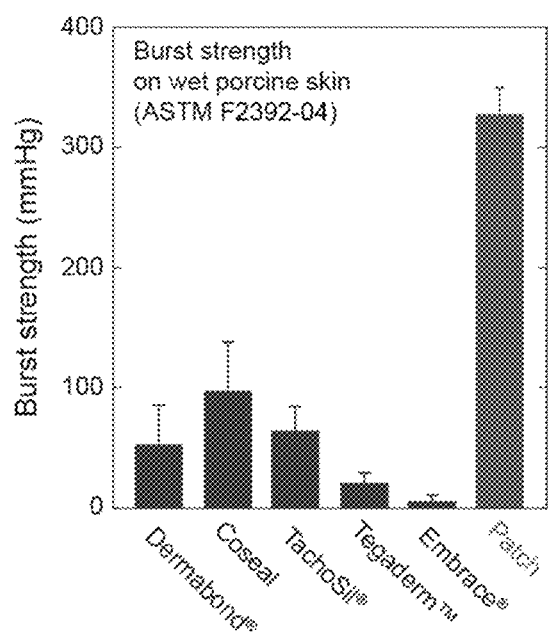

Upon hydration of the shape memory adhesive material 1, its original configuration is elastically recovered by contracting in each direction based on the applied pre-stretch during the fabrication and shape memory process (FIGS. 1 and 3). In the fully swollen equilibrium state, the dimensional shrinkage $\lambda_{patch}^{shrink}=(\lambda_{patch}^{pre})^{-1}$ (FIGS. 8A-B) and mechanical stress (FIGS. 9A-B) generated by contraction of the shape memory adhesive material 1 follows the theoretical predictions both for isotropically (i.e., $\lambda_{patch}^{pre1}=\lambda_{patch}^{pre2}$) and anisotropically (i.e. $\lambda_{patch}^{pre1}\neq\lambda_{patch}^{pre2}$) shape memory adhesive materials 1. This predictive and fully tunable shape memory behavior of the proposed structures originates from the unique advantages of the hydration-based shape memory mechanism and highly programmable fabrication process.

Adhesion Performance of the Shape Memory Adhesive Material

The present invention shape memory adhesive material 1 is configured to form rapid and robust adhesion, even on wet surfaces (e.g., within 5 seconds) owing to its dry adhesive layer 1 fabrication. To characterize the adhesion performance of the shape memory adhesive material 1, four standard characterizations were performed, including 180-degree peel test (ASTM F2256) to measure interfacial toughness, lap-shear test (ASTM F2255) to measure shear strength, wound closure strength test (ASTM F2458-05) to measure wound closure strength, and burst strength test (ASTM F2392-04) to measure burst strength (FIG. 10A-D).

The present invention shape memory adhesive material 1 demonstrated superior adhesion performance compared to existing tissue adhesives and wound dressings including cyanoacrylate-based Dermabond®, polyethylene-glycol-based Coseal, fibrin-based Tachsil®, Tegaderm™, and Embrace® with interfacial toughness over 350 J m$^{-2}$, shear strength over 115 kPa, wound closure strength over 7 N, and burst strength over 310 mmHg (FIG. 11A-D).

Materials and Methods for an Example Embodiment

Figure 12:
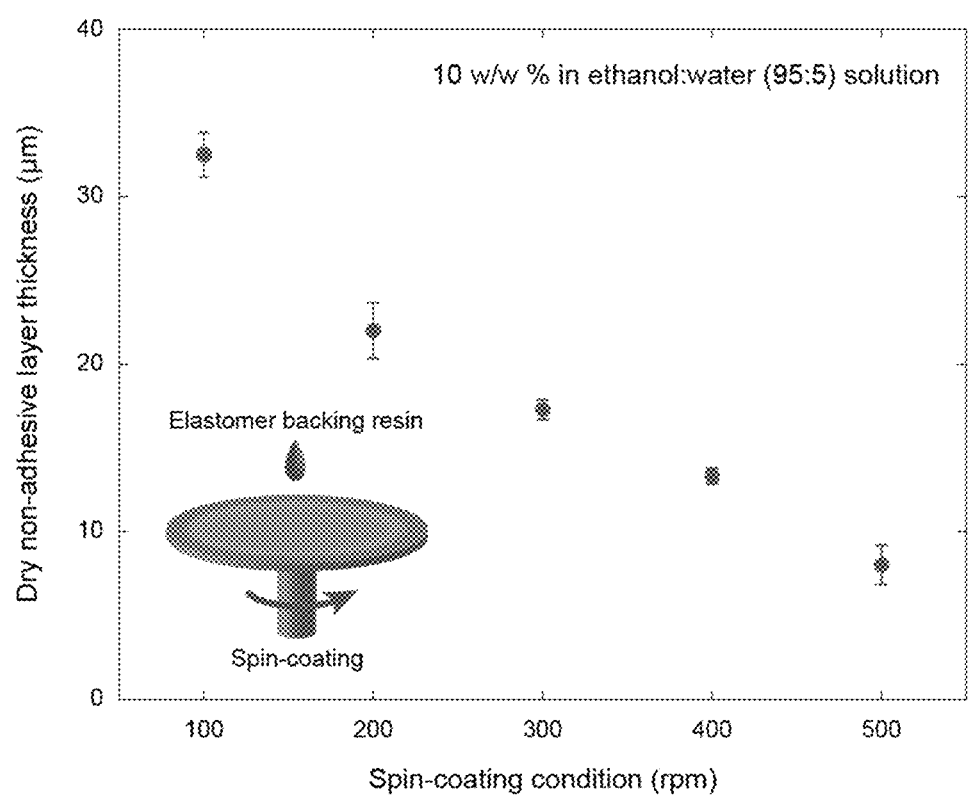
FIG. 12 schematically illustrates spin-coating of an elastomer backing layer according to an embodiment of the present invention. Values represent the mean and the standard deviation (n=4).

Preparation of a shape memory bioadhesive patch. To prepare the bioadhesive patch, chitosan (HMC+Chitoscience Chitosan 95/500, 95% deacetylation, 2 w/w %), acrylic acid (AAc; 30 w/w %), α-ketoglutaric acid (0.2 w/w %), and poly(ethylene glycol methacrylate) (PEGDMA; Mn=550, 0.03 w/w %) were dissolved in deionized water. Then, 5 mg of acrylic acid N-hydroxysuccinimide ester (AAc-NHS) was added into 1 mL of the stock solution. Right after the addition of AAc-NHS, the mixture was cured in a UV chamber (284 nm, 10 W power) for 30 min. As a non-adhesive polymer backing resin, 10 w/w % hydrophilic polyurethane (HydroMed™ D3, Advansource Biomaterials) dissolved in ethanol/water mixture (95:5 v/v) was spin-coated on the as-prepared bioadhesive at 400 rpm for 30 sec and dried completely. Notably, the thickness of the non-adhesive polymer backing can be controlled by adopting different spin-coating condition (FIG. 12). After introducing the non-adhesive polymer backing resin, the shape memory bioadhesive patch was fabricated following the abovementioned five step process. The prepared shape memory bioadhesive patches were sealed in plastic bags with desiccant (silica gel packets) and stored at =20° C. before use.

Mechanical tests. For tissue samples stored more than 10 min before mechanical tests, the samples were covered with a large amount of 0.01 w/v % sodium azide solution (in PBS) spray and sealed in plastic bags to prevent degradation and dehydration of the tissues. Unless otherwise indicated, the shape memory bioadhesive patches were applied after washout of the target tissue surface with PBS followed by 5 sec pressing (with 1 kPa pressure applied by either mechanical testing machine or equivalent weight). A computer-controlled mechanical testing machine (2.5 kN load-cell, Zwick/Roell Z2.5) was used for all mechanical tests following the corresponding ASTM standards (FIG. 10). Hydrophilic nylon filters (1 μm pore size, TISCH Scientific) were applied as a stiff backing for the patches. Poly(methyl methacrylate) films (with a thickness of 50 μm; Goodfellow) were applied using cyanoacrylate glue (Krazy Glue) as a stiff backing for the tissues.

Statistical analysis. MATLAB software was used to assess the statistical significance of all comparison studies in this work. Data distribution was assumed to be normal for all parametric tests, but not formally tested. In the statistical analysis for comparison between multiple samples, one-way ANOVA followed by Tukey's multiple comparison test were conducted with the threshold of $*p \leq 0.05$, $p \leq 0.01$, and $*p \leq 0.001$. In the statistical analysis between two data groups, a two-sample Student's t-test was used, and the significance threshold was placed at $*p \leq 0.05$, $p \leq 0.01$, and $*p \leq 0.001$.

The present invention provides a new type of shape memory adhesive that overcomes existing limitations of adhesive materials which are (a) incapable of forming robust bonding in wet environments and (b) incapable of providing tunable mechanical modulation. In particular, the present shape memory adhesive material synergistically absorbs fluid in an environment (e.g., from a wet tissue surface), forms instant temporary crosslinking, forms fast covalent crosslinking between the shape memory adhesive material and the wet surfaces, and elastically recovers its original configuration in each direction upon absorbing the fluid and transforming from the pre-stretched dry glass state to the hydrated rubber state. This hydration of the shape memory adhesive material results in the material recovering its original configuration by contracting in each direction based on the applied pre-stretch during the fabrication and shape memory process. As such, the shape memory behavior is fully tunable to provide predictable and programmable mechanical modulation of underlying surfaces on which the shape memory adhesive material is adhered.

What is claimed is:

1. A dry shape memory adhesive material for adhering one or more target surfaces comprising:
    a dry adhesive layer comprising one or more hydrophilic polymers, one or more amine coupling groups, and one or more crosslinkers;
    the dry adhesive layer having a top surface, a bottom surface, a thickness measured from the top surface to the bottom surface, a length, and width;
    the dry adhesive layer having a pre-stretched configuration in length and width that is greater in length and width than an original configuration prior to pre-stretching;
    wherein the dry shape memory adhesive material has a liquid content such that placement of one or more of the top and/or bottom surfaces of the dry adhesive layer in contact with the one or more target surfaces in the presence of fluid causes the dry adhesive layer to (a) absorb at least a portion of the fluid, swell in volume and transform to a hydrated rubbery state, and form physical and covalent crosslinks on the one or more target surfaces, and (b) contract in length and/or width from the pre-stretched configuration to about the original configuration.

2. The dry shape memory adhesive material of claim 1, further comprising at least one backing layer disposed on the top surface.

3. The dry shape memory adhesive material of claim 2, further comprising a backing layer removably disposed on the bottom surface.

4. The dry shape memory adhesive material of claim 1, wherein the one or more hydrophilic polymers are selected from polyacrylic acid, polyacrylamide, polyvinyl alcohol, polyhydroxy ethyl methacrylate, polyethylene glycol, polyvinyl pyrrolidone, polystyrene sulfonate, casein, albumin, gelatin, collagen, chitosan, hyaluronic acid, alginic acid, oxidized alginate, pectin, and combinations thereof.

5. The dry shape memory adhesive material of claim 1, wherein the one or more amine coupling groups are selected from N-hydroxysuccinimide ester, N-hydroxysulfosuccinimide ester, aldehyde, imidoester, epoxide, isocyanate, catechol, and combinations thereof.

6. The dry shape memory adhesive material of claim 1, wherein the one or more crosslinkers are selected from gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof.

7. The dry shape memory adhesive material of claim 2, wherein the backing layer is fabricated of one or more of polyurethanes, silicone rubbers, styrene-butadiene-styrene copolymers, butyl rubbers, latex rubbers, and/or hydrogels.

8. The dry shape memory adhesive material of claim 1, wherein the dry adhesive layer comprises an interpenetrating network of chitosan and poly(acrylic acid) (PAA) grafted with N-hydroxysuccinimide (NHS) ester and one or more dry hydrophilic polyurethane backing layers disposed on one or more of the top and/or bottom surfaces of the dry adhesive layer.

9. The dry shape memory adhesive material of claim 1, wherein the dry adhesive layer has a Young's modulus in its hydrated rubbery state that is at least two orders of magnitude lower than the dry adhesive layer Young's modulus in the dry state.

10. The dry shape memory adhesive material of claim 1, wherein the dry shape memory adhesive material is in the form of a sheet, tape, patch, or film.

11. The dry shape memory adhesive material of claim 1, wherein the dry shape memory adhesive material is biodegradable.

* * * * *